United States Patent
Ok et al.

(10) Patent No.: US 10,010,396 B2
(45) Date of Patent: Jul. 3, 2018

(54) MULTILAYER COMPOSITE MATERIALS VIAS

(71) Applicant: Second Sight Medical Products, Inc., San Fernando, CA (US)

(72) Inventors: Jerry Ok, Canyon Country, CA (US); Alfred E Mann, Las Vegas, NV (US)

(73) Assignee: Second Sight Medical Products, Inc., Sylmar, CA (US)

( * ) Notice: Subject to any disclaimer, the term of this patent is extended or adjusted under 35 U.S.C. 154(b) by 350 days.

(21) Appl. No.: 14/219,194

(22) Filed: Mar. 19, 2014

(65) Prior Publication Data
US 2015/0265396 A1    Sep. 24, 2015

(51) Int. Cl.
| | |
|---|---|
| *A61F 2/06* | (2013.01) |
| *A61F 2/00* | (2006.01) |
| *A61L 27/04* | (2006.01) |
| *A61L 27/50* | (2006.01) |

(52) U.S. Cl.
CPC .......... *A61F 2/0095* (2013.01); *A61L 27/047* (2013.01); *A61L 27/50* (2013.01); *A61F 2210/0076* (2013.01); *A61L 2430/16* (2013.01); *Y10T 428/24273* (2015.01)

(58) Field of Classification Search
CPC ..... A61N 1/36046; A61N 1/0543; A61F 2/14; A61F 9/08; A61F 9/00727
See application file for complete search history.

(56) References Cited

U.S. PATENT DOCUMENTS

| | | | |
|---|---|---|---|
| 4,628,933 A | 3/1986 | Michelson | |
| 4,573,481 A | 12/1986 | Bullara | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 2005/0105860 A1* | 5/2005 | Oono | G02B 6/4206 385/88 |
| 2006/0225274 A1* | 10/2006 | Greenberg | A61N 1/0551 29/846 |
| 2008/0290494 A1* | 11/2008 | Lutz | B81B 3/0005 257/690 |

FOREIGN PATENT DOCUMENTS

EP    0589813    * 3/1994

* cited by examiner

*Primary Examiner* — Thomas J Sweet
*Assistant Examiner* — Tiffany Shipmon
(74) *Attorney, Agent, or Firm* — Scott Dunbar

(57) ABSTRACT

Novel multilayer composite material vias for biological implants are disclosed. The vias comprise two metals, so that the metal more compatible with biological environments is on one end of the via, and the metal more compatible with fabrication of a hermetic package is on the other end of the via.

6 Claims, 3 Drawing Sheets

MULTILAYER COMPOSITE MATERIALS VIAS

TECHNICAL FIELD

The present disclosure relates to composite via structures. More particularly, it relates to multilayer composite material vias.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
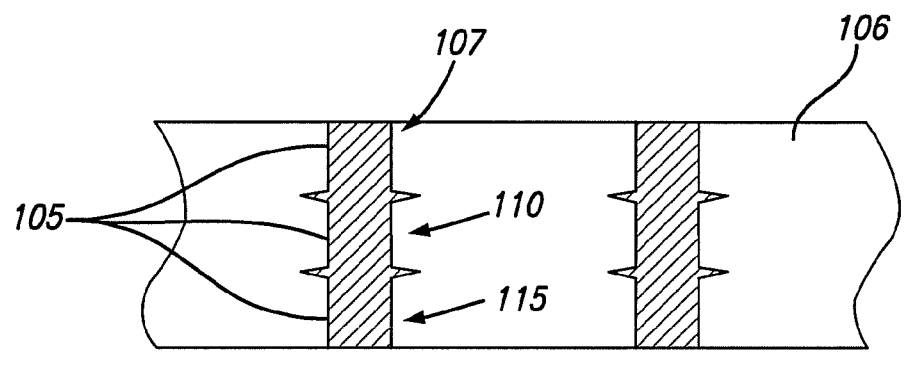
FIG. 1 illustrates a traditional via with one metal.

In a first aspect of the disclosure, a multilayer composite material is described, the multilayer composite material comprising: an insulating substrate having a first surface and a second surface; at least one via defined in the insulating substrate, wherein the at least one via comprises at least one layer of a first metal; and at least one layer of a second metal different from the first metal, and wherein the at least one via forms a continuous path from the first surface to the second surface.

DETAILED DESCRIPTION

High Temperature Co-fired Ceramic (HTCC) is a popular material choice for hermetic packaging due to its desirable electrical properties, high mechanical strength and good thermal conductivity. Hermetic packages are airtight, or otherwise impervious to air or other gases.

The use of platinum as an HTCC via material makes process control difficult due to the catalytic nature of platinum, particularly in reducing firing atmospheres. Platinum reactivity may result in varying degrees of degradation in an HTCC via. This can lead to problems with hermeticity and electrical resistance through the vias. Loss of hermeticity in post processing (e.g. brazing in a reducing atmosphere) is also a danger.

The present disclosure describes a multilayer composite material via that unlike traditional multilayer vias is constructed using more than one metal paste system to fill the via layers. Using more than one metal allows the use of different or complementary properties possessed by different metals.

For example, tungsten is a metal with desirable properties as it is robust and not as reactive as platinum. A composite via structure can take advantage of the robustness of the tungsten system. The process for firing the tungsten system is very robust and insensitive to variation normally occurring during said processing. On the other hand, the catalytic properties of platinum make the platinum material very sensitive to process variation particularly in the area of hermetic sealing.

Tungsten can work very well in terms of hermeticity. The tungsten via is also hermetically stable through extreme post processing conditions (e.g. vacuum braze). The platinum via is not as stable. However, the platinum via can be much more biocompatible and electrochemically stable, resisting corrosion, which makes it suitable for contact with body fluids. The tungsten via readily corrodes in operation when in direct contact with body fluids.

Therefore, in one embodiment of the present disclosure, a composite material construction of the HTCC via takes advantage of the benefits of platinum and tungsten while avoiding their disadvantages.

The side of the substrate that will face the outside of a hermetic package enclosure towards the body environment would be platinum-filled via layer. The remainder of the via layers towards the hermetic package enclosure side of the substrate would be tungsten-filled via layers. The invention may incorporate other metals. Platinum may be replaced with other noble and biocompatible metals such as palladium, iridium, titanium, etc. Tungsten may be replaced with molybdenum or a tungsten-molybdenum mixture.

In such a way, the tungsten side makes use of the durability of tungsten, while platinum is used for its stability in a biological environment, such as for example, biological implants in human bodies.

The vias described in the present disclosure may be fabricated in a variety of ways, for example through providing a first ceramic sheet; forming holes in the sheet; inserting a conductive thick film paste in the hole; laminating the first ceramic sheet and forming a ceramic substrate with a second and third ceramic sheets attached to the upper and lower surfaces of the first ceramic sheet; firing the laminated ceramic substrate to sinter it and cause the metallic paste to form a metallic via, thereby forming a hermetic seal around the metalized via; and finally removing the second and third ceramic sheets in order to expose the metalized via. This method is described, for example, in U.S. Pat. No. 8,555,271, the disclosure of which is incorporated herein by reference in its entirety.

For example, as visible in FIG. 1, a traditional via (105) in a ceramic body (106) may be made of tungsten and comprise three layers (107, 110, 115).

Figure 2:
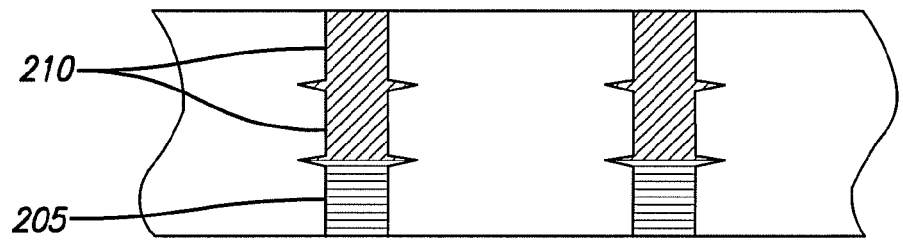
FIG. 2 illustrates one embodiment of a via with two metals.

A via according to one embodiment of the present disclosure, as illustrated in FIG. 2, may comprise a layer of platinum (205), and two layers of tungsten (210).

Figure 3:
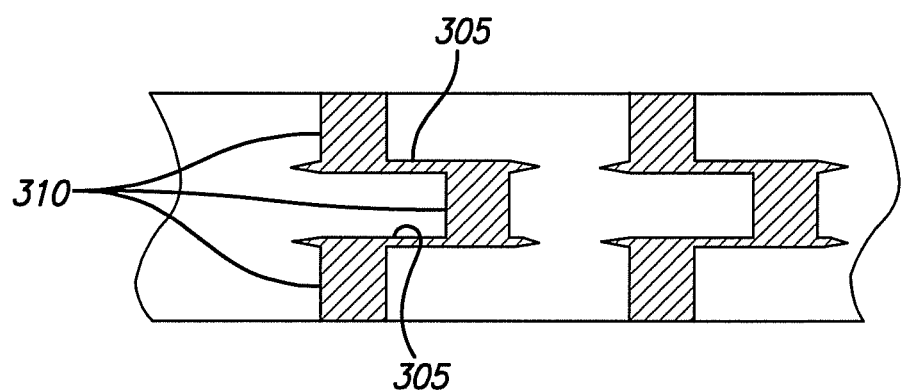
FIG. 3 illustrates a traditional via with one metal and interlayer circuitry.

According to another example, a traditional via may be made, as visible in FIG. 3, by three layers of tungsten (310) and interlayer circuitry also made of tungsten (305).

Figure 4:
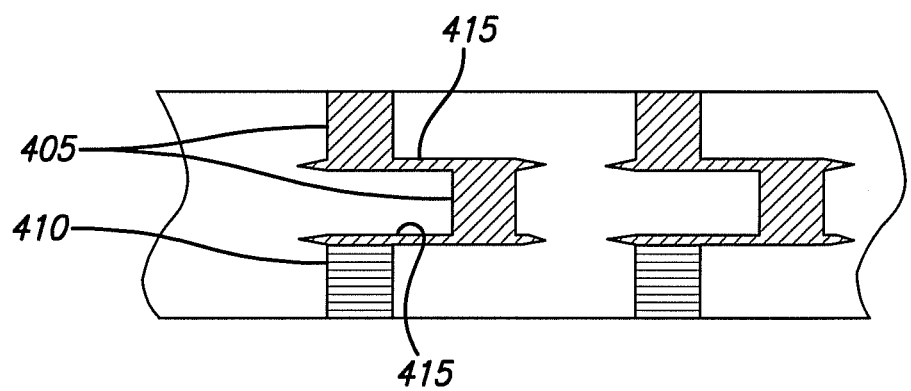
FIG. 4 illustrates one embodiment of a via with two metals and interlayer circuitry.

A via according to one embodiment of the present disclosure, as illustrated in FIG. 4, may comprise a layer of platinum (410), and two layers of tungsten (405), with interlayer circuitry also made of tungsten (415).

Figure 5:
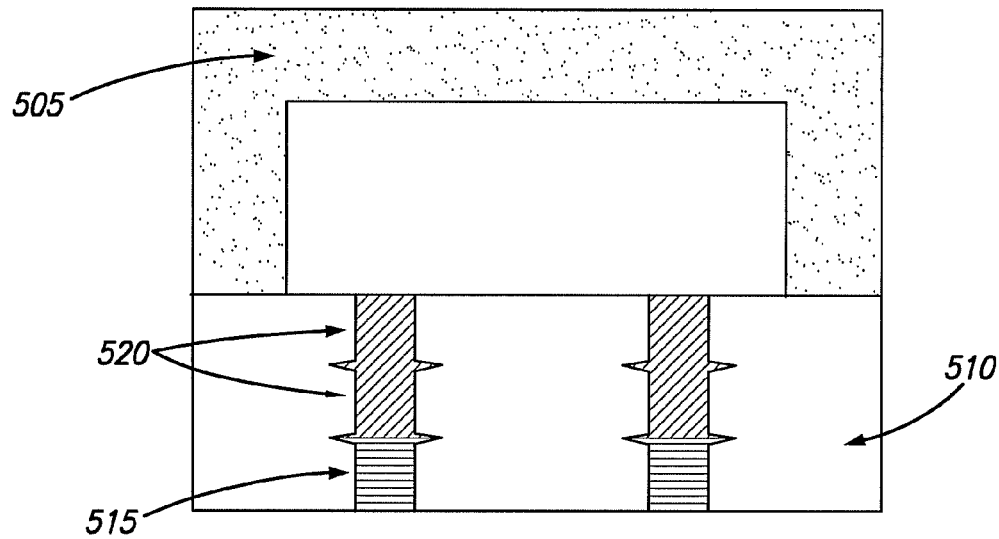
FIG. 5 illustrates one embodiment of a hermetic package.

According to one embodiment of the disclosure, as illustrated in FIG. 5, a hermetic package may comprise a metal container (505) and a substrate (510) through which the vias can be defined. The via may comprise one layer of platinum (515) and two layers of tungsten (520). In such a package the substrate (510) may be brazed to the metal container (505). Titanium nickel braze is suitable for such a purpose. The substrate may be only 0.5 mm in thickness or thinner and remain hermetic. The feedthroughs may have a center to center pitch of 0.7 mm or less.

Figure 6:
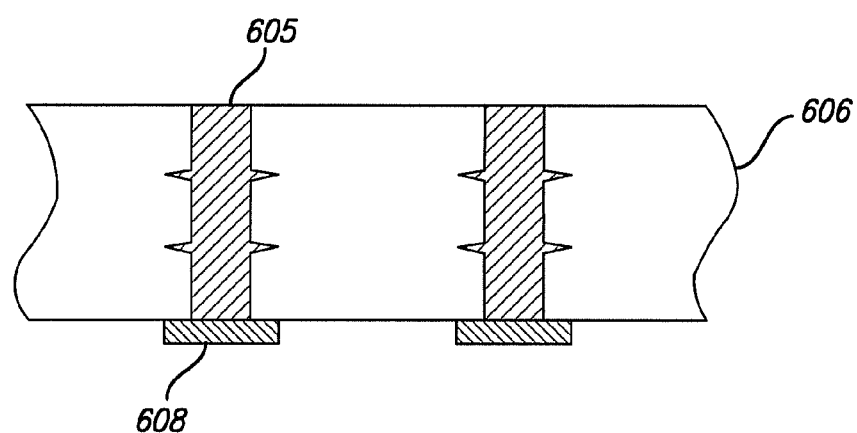
FIG. 6 illustrates an alternate embodiment where a metal via is protected by a biocompatible cap.

FIG. 6 shows an alternate embodiment where the ceramic substrate (606) includes a via (605) of a first metal, tungsten for example, and a cap layer (608) is applied to the body facing side of the ceramic substrate (606) of a second metal, for example platinum. In this embodiment the cap layer (608) must be sufficiently dense to seal the tungsten via. This can be accomplished by electroplating platinum, applying platinum by ion beam assisted deposition, or other methods that result in a dense platinum layer. The cap layer may also function as a metal trace for redirecting an electrical connection to the via.

The hermetic package may be used in biological implants, for example retinal implants which aid vision.

The vias of the present disclosure comprise at least two metals, so that the metal more compatible with biological environments is on one end of the via, in the biological environment, and the metal more compatible with fabrication, such as High Temperature Co-fired Ceramic and hermetic packages, is on the other end of the via.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A multilayer composite material comprising:
   a ceramic insulating substrate having at least two layers, and an inside surface and an outside biocompatible surface;
   at least one via defined in the insulating substrate, wherein the at least one via comprises
      at least one layer of a first metal paste, including a first metal; and
      at least one layer of a second metal paste, including a second metal different from the first metal; and
      a least one interlayer circuit between two layers of the insulating substrate;
      wherein the at least one via forms a hermetically sealed continuous electrical path from the inside surface to the outside biocompatible surface.

2. The multilayer composite material of claim 1, wherein the first metal paste comprises platinum and the second metal paste comprises tungsten.

3. The multilayer composite material of claim 1, wherein the first metal paste comprises platinum, the interlayer circuit is tungsten and the second metal paste comprise tungsten.

4. The multilayer composite material of claim 3, wherein metal on the first surface is platinum and metal on the second surface is tungsten.

5. The multilayer composite material of claim 4, wherein the hermetic package is suitable for implantation in a human or animal body.

6. The multilayer composite material of claim 1, wherein the multilayer composite material forms at least one hermetic wall of a hermetic package.

\* \* \* \* \*